US006312401B1

(12) United States Patent
Smith

(10) Patent No.: US 6,312,401 B1
(45) Date of Patent: Nov. 6, 2001

(54) COLLAPSIBLE CERVICAL TRACTION DEVICE

(76) Inventor: David W. Smith, 4668 4th St., #2, La Mesa, CA (US) 91941

( * ) Notice: Subject to any disclaimer, the term of this patent is extended or adjusted under 35 U.S.C. 154(b) by 0 days.

(21) Appl. No.: 09/655,039

(22) Filed: Sep. 5, 2000

(51) Int. Cl.[7] .......... A61F 5/00

(52) U.S. Cl. .......... 602/32; 482/142; 601/122

(58) Field of Search .......... 602/32, 36, 38; 601/115, 116, 123, 125, 128; 482/140, 142, 148

(56) References Cited

U.S. PATENT DOCUMENTS

| | | | | |
|---|---|---|---|---|
| 1,322,720 | * | 11/1919 | Noble | 601/115 |
| 4,193,394 | * | 3/1980 | Everett | 601/122 |
| 5,573,485 | * | 11/1996 | Geschwender | 482/142 |
| 5,634,887 | * | 6/1997 | Fortier | 601/122 |
| 5,913,758 | * | 6/1999 | Nunez | 482/142 |

* cited by examiner

*Primary Examiner*—Michael A. Brown
(74) *Attorney, Agent, or Firm*—Charles C. Logan, II

(57) ABSTRACT

A collapsible cervical traction device having an elongated primary support leg and a elongated secondary support leg that are pivotally connected to each other so that they are collapsible toward each other. Each support leg has a transversely extending foot member at its rear end. An elongated body support beam has its front end pivotally connected to the top wall of the primary support leg and it has a plurality of laterally spaced roller assemblies attached to its side walls at longitudinally spaced intervals along its length. A neck support assembly is removably received in a tubular sleeve that is pivotally mounted on the front end of the primary support leg. The neck support assembly has a Y-shaped support member having foam cushion members mounted on its upwardly extending arms. The cushion members function to align the neck of a person using the cervical traction device and also functions to elongate the spacing between the neck vertebrae and hold them in traction when the neck support assembly pivots forwardly and downwardly.

9 Claims, 2 Drawing Sheets

COLLAPSIBLE CERVICAL TRACTION DEVICE

BACKGROUND OF THE INVENTION

The invention relates to physical therapy devices and more specifically a physical therapy device that can be safely used by an individual to place their neck in traction for short periods of time.

A significant portion of the population suffer from back and neck pain. Sometimes this is caused by accidents and at other times it occurs due to the natural ageing process of the body and its loss of flexibility. Also stress plays a major role in producing tension that is stored in the muscles of the back and neck.

There are several back therapy machines presently on the market and some of these provide minor relief for a person having neck pain. None of the existing physical therapy devices adequately function to allow a person to stretch the neck vertebrae further apart from each other in a temporary traction state when using the device alone.

It is an object of the invention to provide a novel cervical traction device that allows an individual to lengthen the spacing between the neck vertebrae and place their neck in a temporary state of traction.

It is another object of the invention to provide a novel cervical traction device that also provides some relief and extension of the spacing between the vertebrae of the back to counteract the normal daily nature of having ones back in a total state of compression when one is walking or sitting.

It is also an object of the invention to provide a novel cervical traction device that is collapsible and easily stored out of sight when not in use.

It is an additional object of the invention to provide a novel cervical traction device that is economical to manufacture and market.

It is a further object of the invention to provide a novel cervical traction device that will aid in relieving tension stored in a person's back and neck areas.

It is also an object of the invention to provide a novel cervical traction device that allows a person to increase flexibility of their back and neck by stretching it in the opposite direction in which it is normally positioned while walking and sitting.

SUMMARY OF THE INVENTION

The novel cervical traction device has a primary support leg to which a secondary support leg is pivotally attached so that they are collapsible towards each other. Each of the leg members has a transversely extending foot member connected to their rear end. An elongated body support beam has its front end pivotally connected to bifurcated bracket arms extending upwardly from the top surface of the primary support leg. Foam roller assemblies are mounted on opposite sides of the body support beam at spaced intervals along its length.

A person using the cervical traction device normally lays with their buttocks and upper leg portions on top of the respective foam roller assemblies. The body support beam normally has its rear end supported in a substantially horizontal position by a support arm that is pivotally connected to the primary support leg. The rear end of the body support beam can be moved to a tilted up position by pivoting the support arm to a secondary position. When it is desired to support the bottom of the person's legs, an extension leg support beam can be telescopically attached to the rear end of the body support beam.

There may be one or more laterally spaced foam roller assemblies mounted adjacent the front end of the primary support leg. The upper portion of the back would normally rest upon these foam roller assemblies. Pivotally connected to the front end of the primary support leg is a bifurcated bracket arm whose bottom ends are secured to a tubular sleeve. This entire structure pivots freely around its pivot pin. A neck support assembly has a Y-shaped member having a post extending from its bottom end. The post is telescopically received in the tubular sleeve. The arms of the Y-shaped member extend upwardly and outwardly in a V-shaped formation. Each has a tubular foam cushion member frictionally held thereon. The spacing between the respective tubular foam cushion members is sufficient to allow a person's neck to seat therebetween and the width between the tubular foam cushion members is such that a person's head is restricted from traveling longitudinal therethrough.

As a person lies on the cervical traction device, their head is placed into position between the tubular foam cushion members of the neck support assembly. The weight of this structure and the additional weight of the person causes a forward and downward pivotal motion that extends the space between the neck vertebrae and places the neck in temporary traction. The process of extending the vertebrae longitudinally from each other and stretching takes place slowly and noninjuriously. It allows for relief from tension and also the normal compression that is produced upon the body during walking and sitting during the day.

DESCRIPTION OF THE PREFERRED EMBODIMENT

Figure 1:
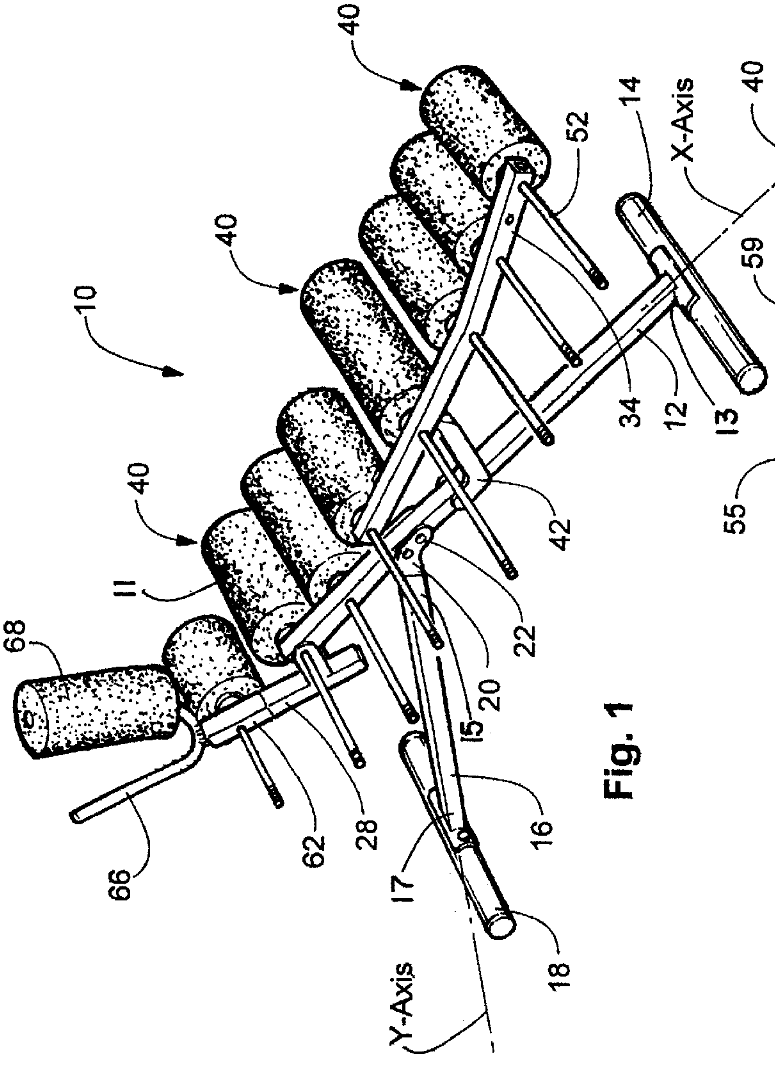
FIG. 1 is a front perspective view of the novel collapsible cervical traction device in its operational position with all of the foam rollers removed from the left side for clarity.

The novel collapsible cervical traction device will now be described by referring to FIGS. 1–7 of the drawings. The collapsible cervical device is generally designated numeral 10. FIG. 1 illustrates the device 10 in its set-up position. It has a tubular primary support leg 12 having a rear end 11 and having a longitudinally extending x-axis with a transversely extending foot member 14 connected to its front end 13. A secondary tubular support leg 16 having a front end 15 and having a longitudinally extending y-axis has a transversely extending foot member 18 connected to its rear end 17. The top end of secondary support leg 16 has bifurcated arms 20 that are pivotally connected to primary support leg 12 by a pivot pin 22. Primary support leg 12 and secondary support leg 16 are preferably made of metal and they would have a substantially square tubular cross section.

Figure 7:
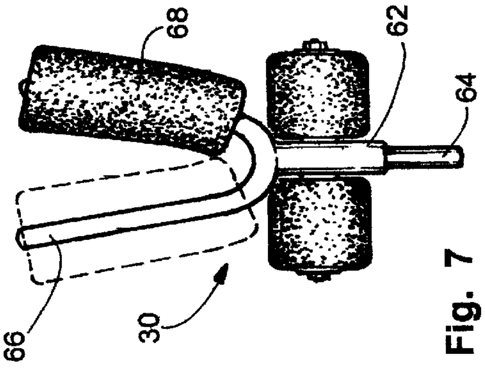
FIG. 7 is a front elevation view of the neck support assembly.

The rear end of primary support leg 12 has laterally spaced transversely extending apertures that receive a pivot pin 24 that extends through the respective apertures in bifurcated bracket arms 26 whose bottom ends are connected to tubular sleeve 28. Neck support assembly 30 is detachably connected to tubular sleeve 28. The structure of neck support assembly 30 is best illustrated in FIG. 7 and it will be described later in detail.

Figure 6:
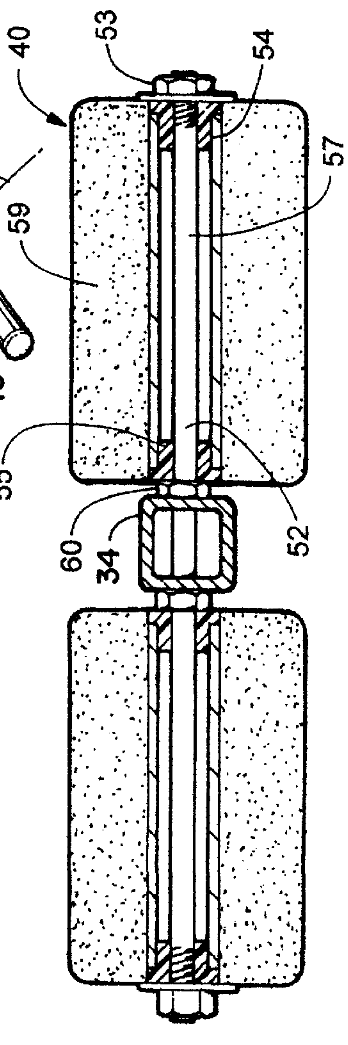
FIG. 6 is a vertical cross section view through one of the sets of foam roller assembly.
Figure 5:
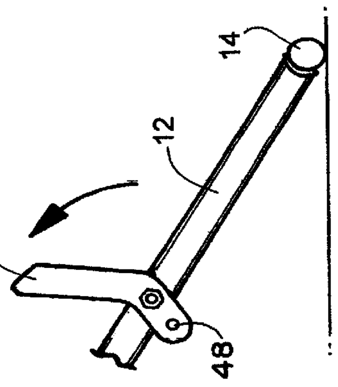
FIG. 5 is a partial left side elevation view illustrating the support arm in an upper position.
Figure 4:
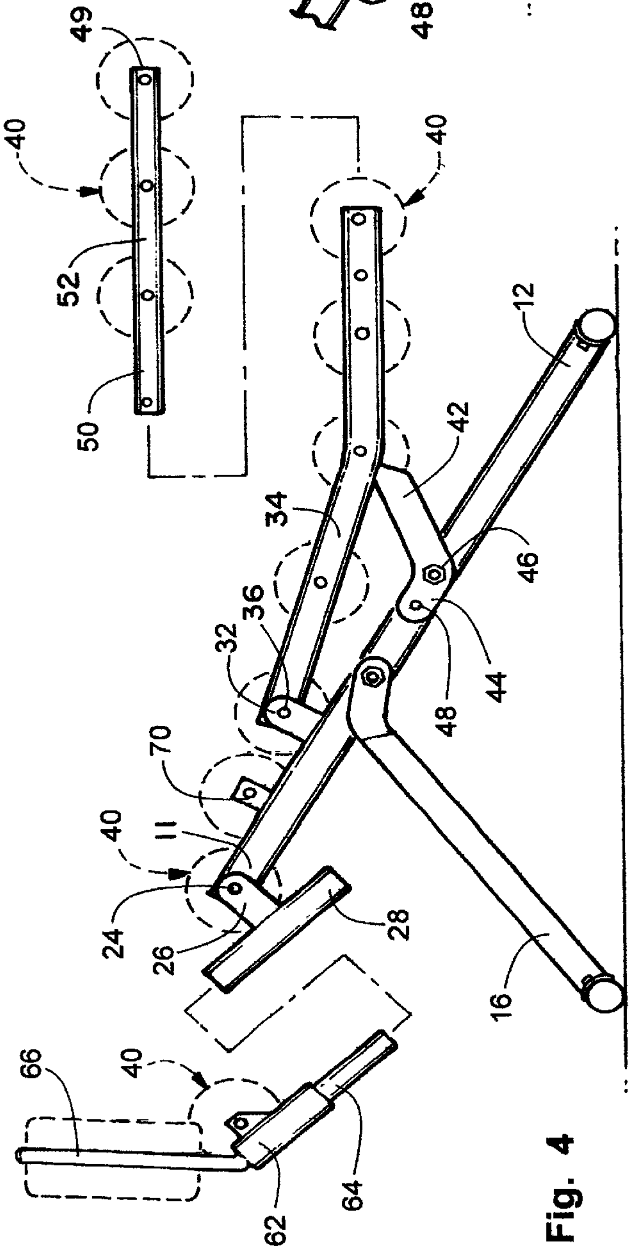
FIG. 4 is a left side elevation view of the collapsible cervical traction device with the foam roller illustrated in phantom lines.

Bifurcated bracket arms 32 have their bottom ends connected to the top surface tubular of primary support leg 12 (see FIG. 4). A tubular body support beam 34 having an obtuse angular bend in it has its rear end pivotally connected to bifurcated bracket arms 32 by a pivot pin 36. Body support beam 44 is preferably made of metal and it would have a substantially square tubular cross section. Five foam plastic roller assemblies 40 are connected to body support beam 34 and their specific structure is best illustrated in FIG. 6 and will be described later. Support arm 42 has bifurcated bracket arms 44 adjacent its front end and it is pivotally connected to primary support leg 12 by pivot pin 46. A pin 48 passes through laterally spaced aligned apertures in primary support leg 12 to keep it in the position illustrated in FIG. 4. The second position of support arm 42 is illustrated in FIG. 5. In this position body support beam 34 would be rotated upwardly a predetermined angle. Pin 48 is then passed through bifurcated bracket arms 44 beneath primary support leg 12 to maintain this position. An extension leg support beam 50 having a front end 49, a rear end 51 and laterally spaced sidewalls 52 can be telescopically inserted into the front end of body support beam 34 when it is desirable to support the legs of the person using the collapsible cervical traction device 10. Three foam plastic roller assemblies 40 are mounted on extension leg support beam 50.

Referring to FIG. 6, the detailed structure of foam plastic roller assemblies 40 will now be described. Each of the foam plastic roller assemblies has a rod 52 extending through laterally spaced aligned apertures in the respective structure to which they are attached. The opposite ends of rod 52 are threaded to receive nuts 53. Bushings 54 and 55 are slid over rod 52 and their outer surfaces is engage tubular core member 57. The tubular foam roller 59 frictionally engages the outer surface of tubular core member 57 so that they rotate as a single unit. Spacers 60 are journaled on rod 52 adjacent the inner ends of the respective tubular plastic foam plastic rollers 59. Essentially all of the foam plastic roller assemblies have the same general construction.

The neck support assembly 30 will now be described by referring to FIG. 7. It has a Y-shaped neck support member 62 having a post 64 connected to its bottom end. Laterally spaced arms 66 each have a tubular foam plastic cushion member 68 frictionally received thereon. A foam plastic roller assembly 40 is also connected to Y-shaped neck support member 62 and it has the same general construction illustrated in FIG. 6. Post 64 is telescopically received in tubular sleeve 28. Bifurcated bracket arms 26 freely rotate around pivot pin 24 allowing the neck support assembly to freely pivot downwardly in response to the weight of the person's head that is using the collapsible cervical traction device. The gripping action of the tubular foam plastic cushion members 68 trap the person's neck and pulls the head into an extended traction position due not only to the weight of the person's head but also the weight of the neck support assembly 30.

Figure 3:
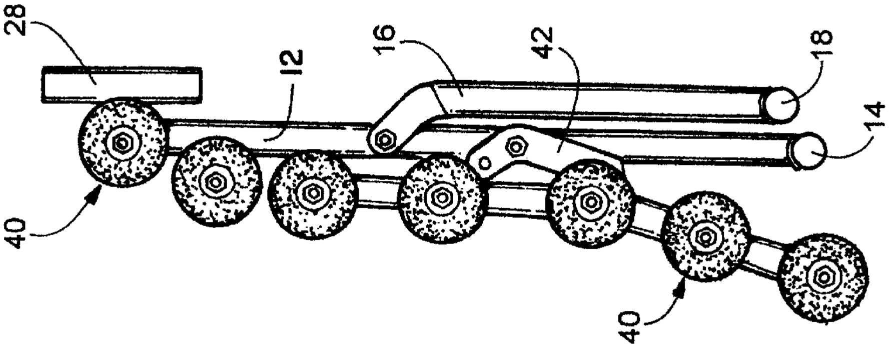
FIG. 3 is a side elevation view of the collapsible cervical traction device in its stored position.
Figure 2:
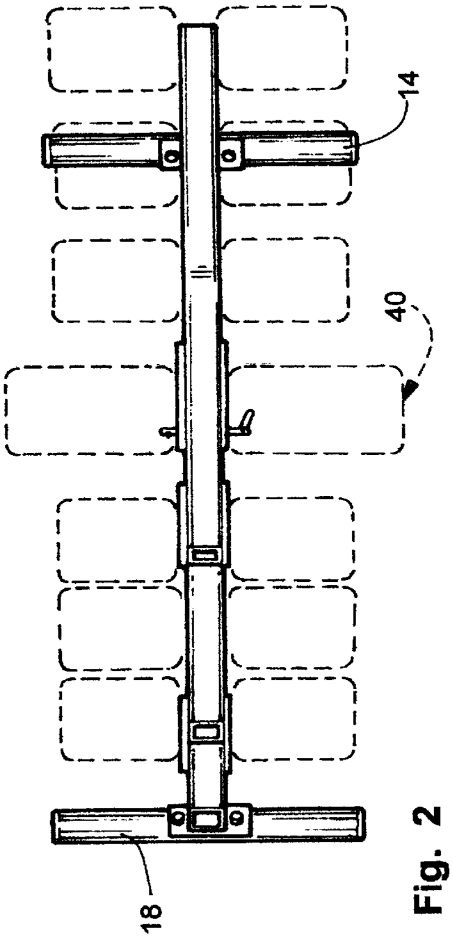
FIG. 2 is a top plan view of the collapsible cervical traction device in its operational position with the foam rollers illustrated in phantom lines.

Bifurcated bracket arms 70 are also connected to the top surface of primary support leg 12 in front of bifurcated bracket arms 32. A foam plastic roller assembly 40 is mounted on the bifurcated arms 70. FIG. 3 shows the collapsible cervical traction device as it appears in its collapsed state for easy storage thereof. FIG. 2 is a top plan view of the collapsible cervical traction device 10 FIG. 1 with the neck support assembly 30 removed and the foam roller assembly 40 shown in phantom.

What is claimed is:

1. A collapsible cervical traction device comprising:

an elongated primary support leg having a front end, a rear end, a top surface, and laterally spaced side walls; a transversely extending foot member is connected to said front end of said primary support leg;

an elongated secondary support leg having a front end and a rear end; a transversely extending foot member is connected to said rear end of said secondary support leg;

means pivotally connecting said front end of said secondary support leg to said primary support leg so that they are collapsible toward each other;

an elongated body support beam having a front end, a rear end, a top surface and laterally spaced side walls; a plurality of roller assemblies are rotationally connected to said side walls at spaced intervals along the length of said body support beams;

means pivotally connecting said rear end of said body support beam to said top surface of said primary support leg;

means for supporting said front end of said body support beam a predetermined height above said front end of said primary leg;

a neck support assembly; and means for pivotally connecting said neck support assembly to said rear end of said primary support leg.

2. A collapsible cervical traction device as recited in claim 1 wherein said primary support leg, said secondary support leg and said body support beams are tubular members.

3. A collapsible cervical traction device as recited in claim 2 wherein said tubular members have a substantially square cross section.

4. A collapsible cervical traction device as recited in claim 2 wherein said tubular members are made of metal material.

5. A collapsible cervical traction device as recited in claim 1 wherein said body support member has two elongated sections each having a different longitudinal axis and they intercept each other at an obtuse angle.

6. A collapsible cervical traction device as recited in claim 1 wherein said roller assemblies have foam plastic rollers.

7. A collapsible cervical traction device as recited in claim 1 further comprising an extension leg support beam having a front end, a rear end, laterally spaced side walls and means for detachably connecting said rear end to said front end of said body support beam.

8. A collapsible cervical traction device as recited in claim 7 further comprising a plurality of roller assemblies rotationally connected to said side walls of said extension leg support beams at spaced intervals along the length of said extension leg support beam.

9. A collapsible cervical traction device as recited in claim 1 further comprising at least one pair of laterally spaced roller assemblies mounted on said primary support leg adjacent said rear end.

* * * * *